(12) United States Patent
Tamburro et al.

(10) Patent No.: US 8,124,827 B2
(45) Date of Patent: Feb. 28, 2012

(54) ABSORBENT CORE

(75) Inventors: Maurizio Tamburro, Sambuceto (IT); Evelina Toro, Chieti (IT); Nicola D'Alesio, Canosa Sannita (IT); Giovanni Carlucci, Chieti (IT)

(73) Assignee: The Procter and Gamble Company, Cincinnati, OH (US)

( * ) Notice: Subject to any disclaimer, the term of this patent is extended or adjusted under 35 U.S.C. 154(b) by 438 days.

(21) Appl. No.: 12/326,130

(22) Filed: Dec. 2, 2008

(65) Prior Publication Data

US 2009/0209932 A1 Aug. 20, 2009

(30) Foreign Application Priority Data

Dec. 7, 2007 (EP) .................................. 07023735

(51) Int. Cl.
*A61F 13/15* (2006.01)
*A61F 13/20* (2006.01)

(52) U.S. Cl. ........................................ 604/368; 604/367

(58) Field of Classification Search .................. 604/383; 428/131, 132, 134, 137

See application file for complete search history.

(56) References Cited

U.S. PATENT DOCUMENTS

| | | | | |
|---|---|---|---|---|
| 3,989,867 | A * | 11/1976 | Sisson | 428/132 |
| 4,950,264 | A * | 8/1990 | Osborn, III | 604/385.08 |
| 6,025,049 | A * | 2/2000 | Ouellette et al. | 428/131 |
| 6,150,002 | A | 11/2000 | Varona | |
| 6,197,404 | B1 | 3/2001 | Varona | |
| 6,838,154 | B1 | 1/2005 | Varona et al. | |
| 2004/0131820 | A1 | 7/2004 | Turner et al. | |
| 2004/0167486 | A1* | 8/2004 | Busam et al. | 604/367 |
| 2008/0125735 | A1 | 5/2008 | Busam et al. | |
| 2008/0167634 | A1 | 7/2008 | Kouta et al. | |

OTHER PUBLICATIONS

European Search Report dated May 27, 2008.

* cited by examiner

*Primary Examiner* — Melanie Hand
(74) *Attorney, Agent, or Firm* — Andres E. Velarde; David M. Weirich

(57) ABSTRACT

Absorbent core for disposable absorbent articles, particularly for the absorption of menses or blood.

15 Claims, 4 Drawing Sheets

ABSORBENT CORE

FIELD OF THE INVENTION

The present invention relates to an absorbent core for absorbent articles, for example sanitary napkins and the like.

BACKGROUND OF THE INVENTION

Absorbent articles for absorption of body fluids such as menses or blood or vaginal discharges are well known in the art, and comprise for example feminine hygiene articles such as sanitary napkins, panty liners, tampons, interlabial devices, as well as wound dressings, and the like. When considering for example sanitary napkins, these articles typically comprise a liquid-pervious topsheet as wearer-facing layer, a backsheet as garment-facing layer and an absorbent core between topsheet and backsheet. The body fluids are acquired through the topsheet and subsequently stored in the absorbent core. The backsheet typically prevents the absorbed fluids from wetting the wearer's garment.

An absorbent core can typically comprise one or more fibrous absorbent material, which in turn can comprise natural fibres, such as for example cellulose fibres, typically wood pulp fibres, synthetic fibres, or combinations thereof.

Absorbent articles can further comprise, typically in the absorbent core, superabsorbent materials, such as absorbent gelling materials (AGM), usually in finely dispersed form, e.g. typically in particulate form, in order to improve their absorption and retention characteristics. Superabsorbent materials for use in absorbent articles typically comprise water-insoluble, water-swellable, hydrogel-forming crosslinked absorbent polymers which are capable of absorbing large quantities of liquids and of retaining such absorbed liquids under moderate pressure. Absorbent gelling materials can be incorporated in absorbent articles, typically in the core structure, in different ways; for example, absorbent gelling materials in particulate form can be dispersed among the fibres of fibrous layers comprised in the core, or rather localized in a more concentrated arrangement between fibrous layers.

Absorbent cores for absorbent articles having a thin structure can further provide an improved immobilization of absorbent gelling materials, particularly when the article is fully or partially loaded with liquid, and an increased wearing comfort. Such thinner structures provide absorbent articles combining better comfort, discreetness and adaptability, such as for example, thin absorbent structures where the absorbent gelling material is located and somehow kept in selected, e.g. patterned regions of the structure itself.

While absorbent articles comprising thin absorbent cores with relatively high amounts of absorbent gelling materials and rather low contents of fibrous materials may have good absorption and retention characteristics to urine, there still remains room for improvement of absorption and retention, particularly towards other body fluids. In particular, menses, blood and vaginal discharges are particularly difficult to be effectively absorbed and retained into absorbent cores containing superabsorbent materials in major amounts since such materials may not show optimal absorption and retention characteristics towards such body fluids.

It is believed that the non-optimal absorption and retention are mainly caused by poor permeability of superabsorbent materials towards menses, blood or vaginal discharges due to the viscosity and/or to the complex nature of these fluids. For example menses and blood are water based fluids comprising components having molecular weights higher than water and also corpuscular components, including red cells, white cells, soluble proteins, cellular debris and mucus, which slow down the absorption of these fluids by superabsorbents. Menses and blood are rather thick, and more difficult to absorb in conventional absorbent structures comprising absorbent gelling materials; moreover, corpuscular components like red cells may decrease the absorption capacity of certain superabsorbent particles. This translates into a slower initial uptake rate of the fluid into the superabsorbent material, and in turn in the absorbent structure comprising the superabsorbent material, which can result in a lower final absorption and retention capacity.

Hence, there is still the need for an improved, thin absorbent core structure for an absorbent article, particularly for absorption of menses or blood or vaginal discharges, which comprises the absorbent gelling material in a non uniform layer stably provided onto a fibrous substrate layer in a better integrated structure, which can take advantage of the peculiarities of the different fibrous and non-fibrous absorbent materials in the absorption and management of these complex body fluids, achieving a better result in terms of fluid acquisition and distribution. Such a structure could also be stably thin, or in any case should not significantly change (for example increase) its thickness upon absorption throughout its normal use.

SUMMARY OF THE INVENTION

The present invention addresses the above needs by providing an absorbent core for an absorbent article intended for absorption of menses or blood or vaginal discharges, which comprises a substrate layer, comprising a first surface and a second surface; the absorbent core further comprises a non uniform layer of absorbent polymer material, comprising a first surface and a second surface; the absorbent core also comprises a layer of a thermoplastic material, comprising a first surface and a second surface, and a cover layer comprising a first surface and a second surface. The second surface of the non uniform layer of absorbent polymer material is in at least partial contact with the first surface of the substrate layer; portions of the second surface of the layer of thermoplastic material are in direct contact with the first surface of the substrate layer and portions of the second surface of the layer of thermoplastic material are in direct contact with the first surface of the non uniform layer of absorbent polymer material, wherein the second surface of the cover layer is in direct contact with the first surface of the layer of thermoplastic material. The substrate layer or the cover layer comprise a fibrous web of fibres substantially randomly oriented with respect to an X-Y plane, and the substrate layer or the cover layer comprises a plurality of discrete regions of fibre reorientation, comprising a plurality of fibres having portions reoriented in a direction substantially orthogonal to the X-Y plane.

DETAILED DESCRIPTION OF THE INVENTION

Figure 1:
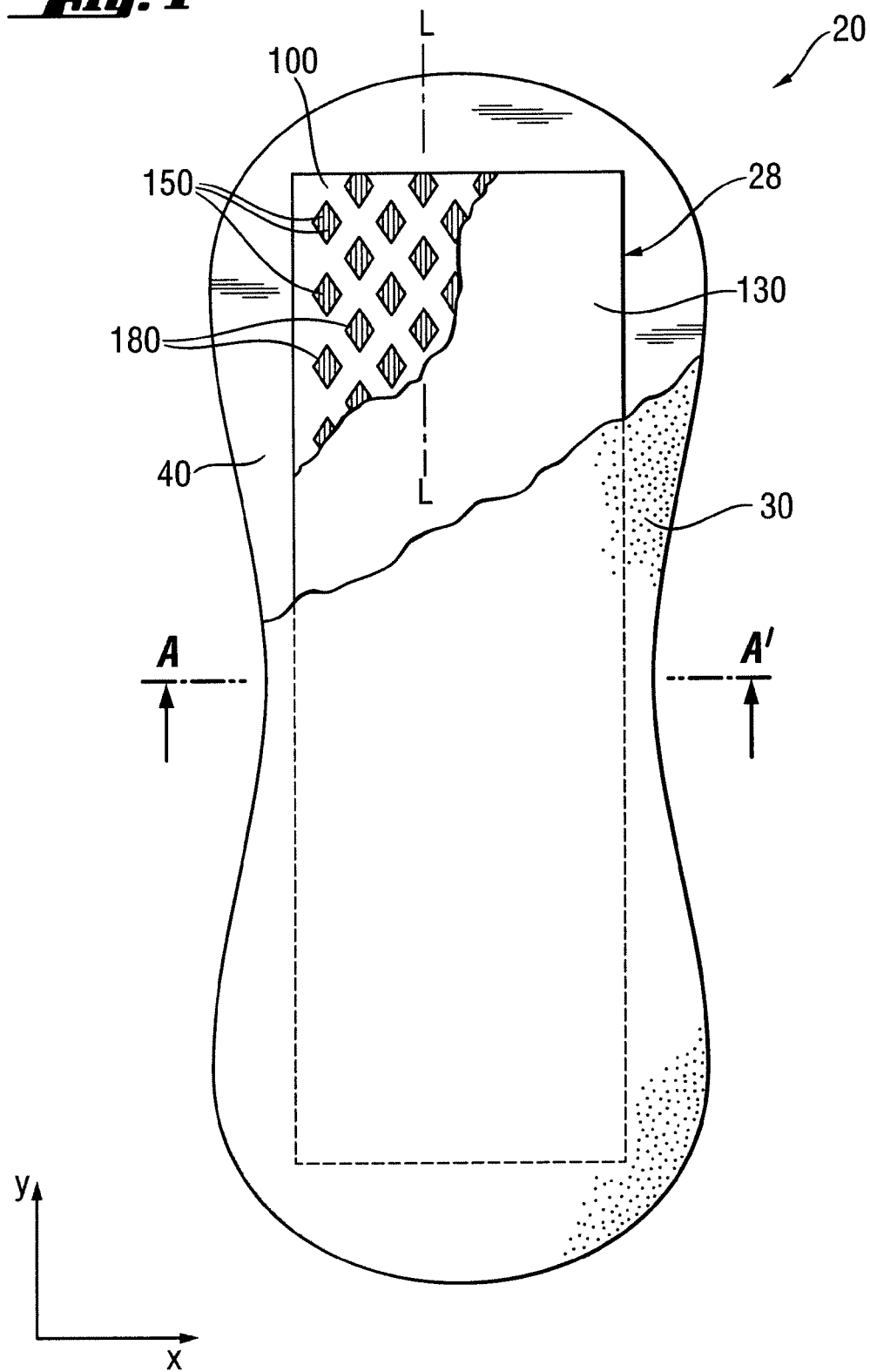
FIG. 1 is a plan view of a sanitary napkin showing an absorbent core according to an embodiment of the present invention, with portions of some constituent elements cut out in order to show underlying elements.

The present invention relates to an absorbent core for absorbent articles such as sanitary napkins, panty liners, tampons, interlabial devices, wound dressings, and the like, which are intended for the absorption of body fluids, such as menses or blood or vaginal discharges. Exemplary absorbent articles in the context of the present invention are disposable absorbent articles. The term "disposable" is used herein to describe articles, which are not intended to be laundered or otherwise restored or reused as an article (i.e. they are intended to be discarded after a single use and preferably to be recycled, composted or otherwise disposed of in an environmentally compatible manner). The absorbent core of the present invention will be herein described in the context of a typical absorbent article, such as, for example, a sanitary napkin 20 as illustrated in FIG. 1. Typically, such articles as shown in FIG. 1 can comprise the elements of a liquid pervious topsheet 30, a backsheet 40 and an absorbent core 28 intermediate said topsheet 30 and said backsheet 40.

In the following description of the invention, the surface of the article, or of each element thereof, which in use faces in the direction of the wearer is called wearer-facing surface. Conversely, the surface facing in use in the direction of the garment is called garment-facing surface. The absorbent article of the present invention, as well as any element thereof, such as, for example the absorbent core, has therefore a wearer-facing surface and a garment-facing surface.

Topsheet

According to the present invention, the absorbent article can comprise a liquid pervious topsheet. The topsheet suitable for use herein can comprise wovens, non-wovens, and/or three-dimensional webs of a liquid impermeable polymeric film comprising liquid permeable apertures. In FIG. 1 the topsheet is indicated with reference numeral 30. For example, the wearer-facing and contacting surface can be provided by a film material having apertures which are provided to facilitate liquid transport from the wearer facing surface towards the absorbent structure. Such liquid permeable, apertured films are well known in the art. They provide a resilient three-dimensional fibre-like structure. Such films have been disclosed in detail for example in U.S. Pat. No. 3,929,135, U.S. Pat. No. 4,151,240, U.S. Pat. No. 4,319,868, U.S. Pat. No. 4,324,426, U.S. Pat. No. 4,343,314, U.S. Pat. No. 4,591,523, U.S. Pat. No. 4,609,518, U.S. Pat. No. 4,629,643, U.S. Pat. No. 4,695,422 or WO 96/00548.

The topsheet for use herein can be a single layer or may have a multiplicity of layers. In an embodiment of the present invention, the topsheet across its full extension can be a single layer, which provides both the wearer-facing surface and the garment-facing surface of the topsheet. Optionally, on the wearer-facing surface of the topsheet but only extending in the peripheral zone of the article an additional layer may be desirable to provide extra softness or extra liquid handling/retaining abilities (this design is usually referred to as "hybrid topsheet"). The topsheet typically extends across the whole of the absorbent structure and can extend into and form part of or all of the preferred but optional side flaps, side-wrapping elements, wings or ears. Also the topsheet can wrap around the absorbent core edges.

The topsheet as a whole shall be compliant, soft feeling, and non-irritating to the wearer's skin. It also can have elastic characteristics allowing it to be stretched in one or more directions. The topsheet may provide for acquisition and transport of fluid from the wearer towards the absorbent core and containment of the absorbent core. In addition to liquid permeability, the topsheet may have a high vapor permeability and/or air permeability.

Absorbent Core

Figure 2:
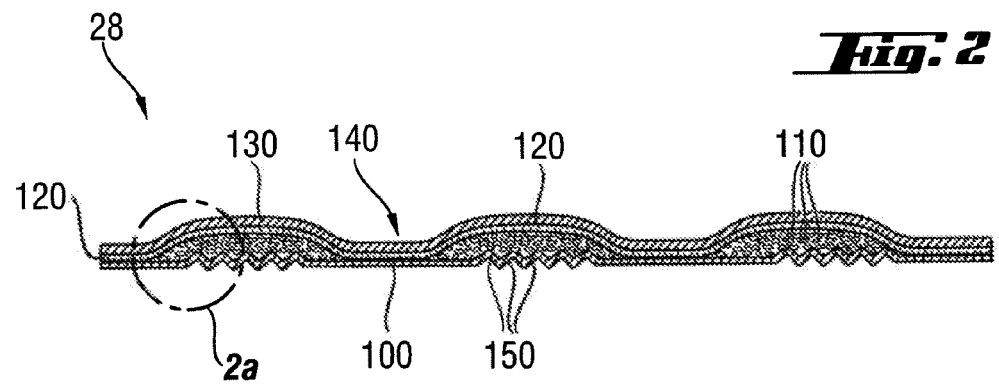
FIG. 2 is a schematic cross section of a portion of an absorbent core according to an embodiment of the present invention.
Figure 2A:
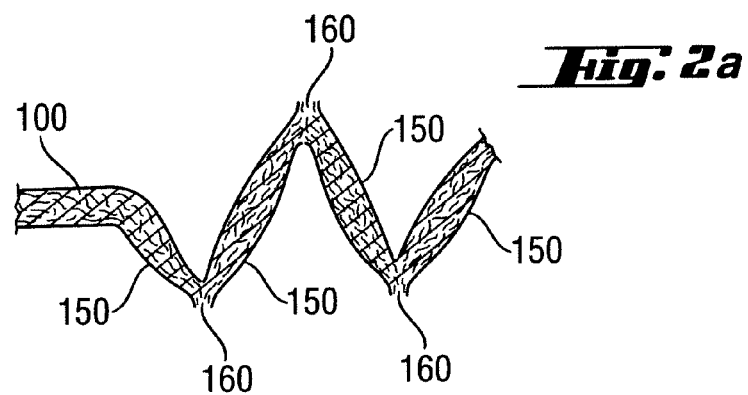
FIG. 2a is a schematic cross section of an element of the absorbent core as illustrated in FIG. 2.
Figure 4:
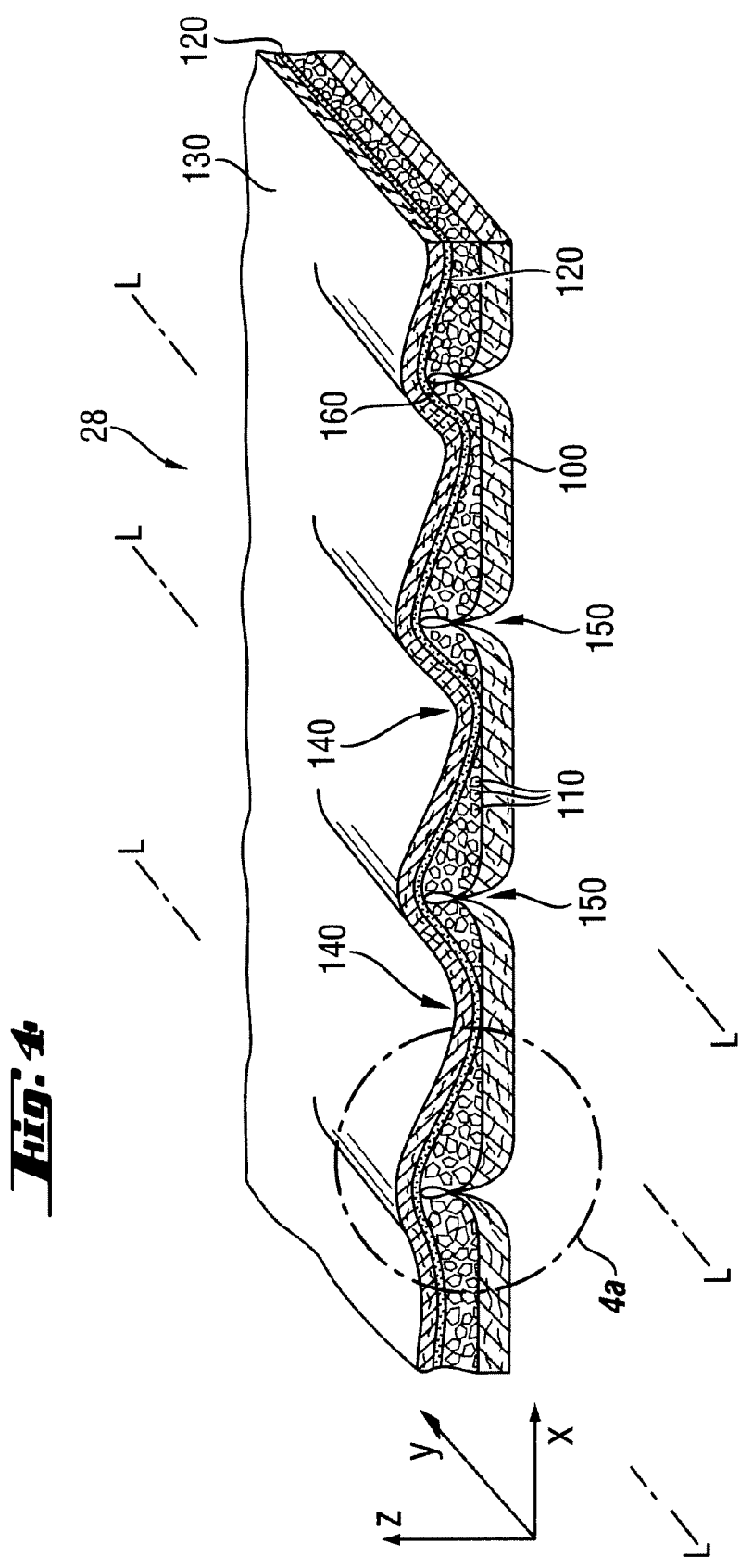
FIG. 4 shows a schematic perspective view, comprising a cross section, of a portion of an absorbent core according to another embodiment of the present invention.

According to the present invention, and as shown for example in the embodiments of FIGS. 2 and 4, the absorbent core 28 comprises a substrate layer 100, absorbent polymer material 110, a layer of thermoplastic material 120, typically for example a layer of fiberized hot melt adhesive 120, and a cover layer 130. The substrate layer 100 and the cover layer 130 can be typically provided from a fibrous material, as will be explained in detail below.

The substrate layer 100 comprises a first surface and a second surface. Conventionally, in the sectional views illustrated in the attached drawings the first surface of each layer can be said to correspond to the top surface, while the second surface corresponds to the bottom surface. At least portions of the first surface of the substrate layer 100 are in contact with a layer of absorbent polymer material 110. This layer of absorbent polymer material 110 can be typically a non uniform layer, and comprises a first surface and a second surface, wherein by "non uniform" it is meant that the absorbent polymer material 110 is distributed over the substrate layer 100 with non uniform basis weight. Conversely, the second surface of the non uniform layer of absorbent polymer material 110 is in at least partial contact with the first surface of the substrate layer 100. According to an embodiment of the present invention, the non uniform layer of absorbent polymer material 110 can be a discontinuous layer that is a layer typically comprising openings, i.e. areas substantially free of absorbent polymer material, which in certain embodiments can be typically completely surrounded by areas comprising absorbent polymer material, as will be explained in more detail later on. Typically these openings have a diameter or largest span of less than about 10 mm, or less than about 5 mm, or about 3 mm, or about 2 mm, or about 1.5 mm and of more than about 0.5 mm, or about 1 mm. At least portions of the second surface of the absorbent polymer material layer 110 are in contact with at least portions of the first surface of the substrate layer material 100. The first surface of the absorbent polymer material 110 defines a certain height of the layer of absorbent polymer material above the first surface of the layer of substrate material 100. When the absorbent polymer material layer 110 is provided as a non uniform layer, typically for example as a discontinuous layer, at least some portions of the first surface of the substrate layer 100 are not covered by absorbent polymer material 110. The absorbent core 28 further comprises a layer of a thermoplastic material 120. This thermoplastic material 120 serves to at least partially immobilize the absorbent polymer material 110.

In a typical embodiment of the present invention the thermoplastic material 120 can be provided as a fibrous layer which is partially in contact with the absorbent polymer material 110 and partially in contact with the substrate layer 100. FIGS. 2 and 4 show such a structure in two exemplary embodiments of the present invention. In this structure the absorbent polymer material layer 110 is provided as a discontinuous layer, a layer of fiberized thermoplastic material 120 is laid down onto the layer of absorbent polymeric material 110, such that the thermoplastic layer 120 is in direct contact with the first surface of the layer of absorbent polymer material 110, but also in direct contact with the first surface of the substrate layer 100, where the substrate layer is not covered by the absorbent polymeric material 110, i.e. typically in correspondence of the openings of the discontinuous layer of the polymer material 120. By "direct contact" it is meant that there is no further intermediate component layer between the layer of thermoplastic material 120 and the other respective layer in direct contact thereto, such as for example a further fibrous layer. It is however not excluded that a further adhesive material can be comprised between the layer of thermoplastic material 120 and the cover layer 130, or the layer of absorbent polymer material 110 or, more typically, the substrate layer 100, such as for example a supplementary adhesive material provided onto the first surface of the substrate layer 100 to further stabilize the overlying absorbent polymer material 110. "Direct contact" can hence be considered to mean in this context a direct adhesive contact between the layer of thermoplastic material 120 and the other respective layer as explained above. This imparts an essentially three-dimensional structure to the fibrous layer of thermoplastic material 120 which in itself is essentially a two-dimensional structure of relatively small thickness (in z-direction), as compared to the extension in x- and y-direction. In other words, the fibrous thermoplastic material layer 120 undulates between the first surface of the absorbent polymer material 110 and the first surface of the substrate layer 100. The areas where the fibrous thermoplastic material 120 is in contact with the substrate layer 100 are the areas of junction 140.

Thereby, the thermoplastic material 120 provides spaces to hold the absorbent polymer material 110 typically towards the substrate layer 100, and thereby immobilizes this material. In a further aspect, the thermoplastic material 120 bonds to the substrate 100 and thus affixes the absorbent polymer material 110 to the substrate 100. Typical thermoplastic materials will also penetrate into both the absorbent polymer material 110 and the substrate layer 100, thus providing for further immobilization and affixation.

Of course, while the thermoplastic materials disclosed herein can provide a much improved wet immobilisation, i.e. immobilisation of absorbent polymer material when the article is wet or at least partially loaded, these thermoplastic materials can also provide a very good immobilisation of absorbent polymer material when the article is dry.

In accordance with an embodiment of the present invention, the absorbent polymer material 110 may also be optionally mixed with fibrous material, which can provide a matrix for further immobilization of the absorbent polymer material. However, typically a relatively low amount of fibrous material can be used, for example less than about 40 weight %, less than about 20 weight %, or less than about 10 weight % of the total weight of the absorbent polymer material 110, positioned within the areas of absorbent polymer material.

Figure 3:
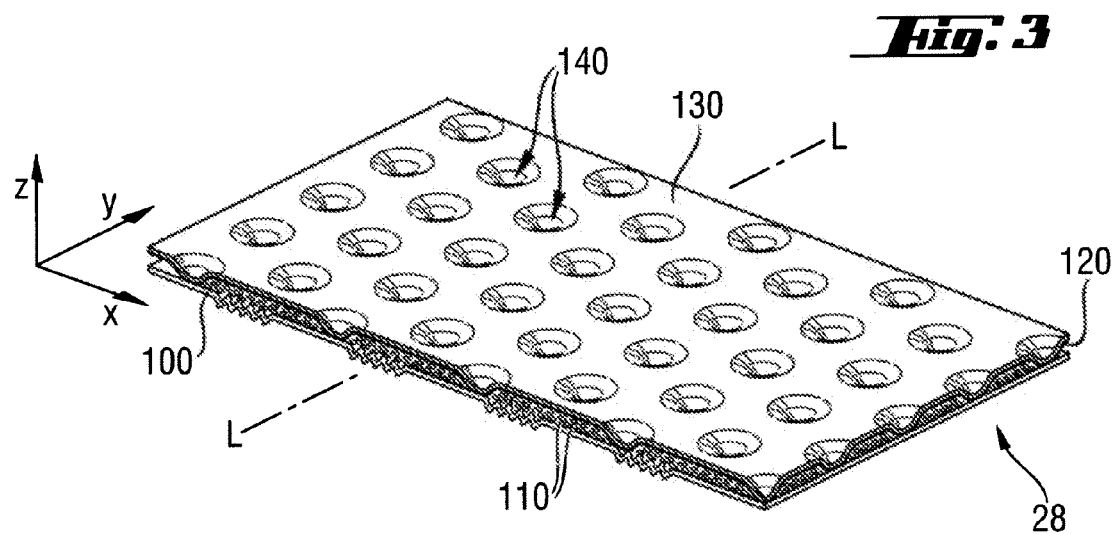
FIG. 3 shows a perspective view of an exemplary absorbent core according to an embodiment of the present invention.

According to an embodiment of the present invention, in a typically discontinuous layer of absorbent polymer material 110 the areas of absorbent polymer material can be connected to one another, while the areas of junction 140 can be areas, which in an embodiment may correspond to the openings in the discontinuous layer of absorbent polymer material, as shown for example in FIG. 3. The areas of absorbent polymer material are then referred to as connected areas. In an alternative embodiment, the areas of junction 140 can be connected to one another. Then, the absorbent polymer material can be deposited in a discrete pattern, or in other words the absorbent polymer material represents islands in a sea of thermoplastic material 120. Hence, in summary, a discontinuous layer of absorbent polymer material 110 may comprise connected areas of absorbent polymer material 110, as e.g. illustrated in FIG. 3, or may alternatively comprise discrete areas of absorbent polymer material 110.

The absorbent core shown in FIGS. 2 and 4 in two different embodiments of the present invention can further comprise a cover layer 130. This cover layer may be provided of the same material as the substrate layer 100, or may be provided from a different material. Suitable materials for the cover layer are for example nonwoven materials, as will be better explained further on. In these embodiments portions of the cover layer 130 bond to portions of the substrate layer 100 via the thermoplastic material 120. Thereby, the substrate layer 100 together with the cover layer 130 provides spaces to immobilize the absorbent polymer material 110.

Figure 5:
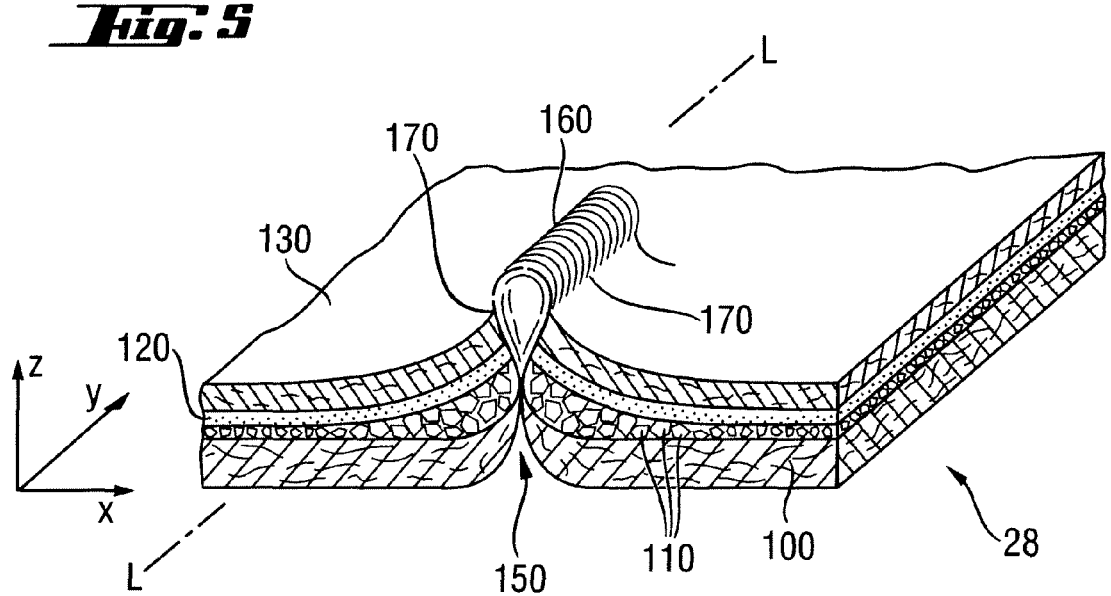
FIG. 5 shows a perspective view of a portion of an absorbent core according to an alternative embodiment of the present invention.

The present invention, and specifically the embodiments described with reference to FIGS. 2, 4 and 5 can be used to provide a storage layer of an absorbent core. However, they can also be used to provide the full absorbent core 28 as illustrated in FIG. 1. In that case, no further materials wrapping the core, such as a top layer and a bottom layer are being used. With reference to the embodiments of FIGS. 2, 4 and 5 the cover layer 130 may provide the function of a top layer and the substrate layer 100 may provide the function of a bottom layer of an absorbent core, wherein top and bottom layers respectively correspond to the body facing and garment facing surfaces of the core 28.

With reference to FIGS. 2 and 4 the areas of direct contact between the thermoplastic material 120 and the substrate material 100 are referred to as areas of junction 140. The shape, number and disposition of the areas of junction 140 will influence the immobilization of the absorbent polymer material 110. The areas of junction can be for example of squared, rectangular or circular shape. Areas of junction of circular shape can have a diameter of more than about 0.5 mm, or more than about 1 mm, and of less than about 10 mm, or less than about 5 mm, or less than about 3 mm, or less than about 2 mm, or less than about 1.5 mm. If the areas of junction 140 are not of circular shape, they can be of a size as to fit inside a circle of any of the diameters given above.

The areas of junction 140 can be disposed in a regular or irregular pattern. For example, the areas of junction 140 may be disposed along lines as shown in FIG. 3. These lines may be aligned with the longitudinal axis of the absorbent core, or alternatively they may have a certain angle in respect to the longitudinal edges of the core. A disposition along lines parallel with the longitudinal edges of the absorbent core 28 might create channels in the longitudinal direction which can lead to a lesser wet immobilization, hence for example the areas of junction 140 can be arranged along lines which form an angle of about 20 degrees, or about 30 degrees, or about 40 degrees, or about 45 degrees with the longitudinal edges of the absorbent core 28. Another pattern for the areas of junction 140 can be a pattern comprising polygons, for example pentagons and hexagons or a combination of pentagons and hexagons. Also typical can be irregular patterns of areas of junction 140, which also can give a good wet immobilization. Irregular patterns of areas of junction 140 can also give a better fluid handling behaviour in case of absorption of menses or blood or vaginal discharges, since fluid can start diffusing in whichever direction from any initial acquisition point with substantially the same probability of contacting the absorbent polymer material in the e.g. discontinuous layer. Conversely, regular patterns might create preferential paths the fluid could follow with lesser probability of actually contacting the absorbent polymer material.

According to the present invention the thermoplastic layer 120 can comprise any thermoplastic material, typically adhesive thermoplastic materials, also referred to as hot melt adhesives. A variety of thermoplastic materials can be suitable to immobilize the absorbent polymer material. Some initially thermoplastic materials may later lose their thermoplasticity due to a curing step, e.g. initiated via heat, UV radiation, electron beam exposure or moisture or other means of curing, leading to the irreversible formation of a crosslinked network of covalent bonds. Those materials having lost their initial thermoplastic behaviour can be herein also understood as thermoplastic materials 120.

Without wishing to be bound by theory it has been found that those thermoplastic materials, i.e. the hot melt adhesives, can be most useful for immobilizing the absorbent polymer material 110, which combine good cohesion and good adhesion behaviour. Good adhesion is critical to ensure that the thermoplastic layer 120 maintains good contact with the absorbent polymer material 110 and in particular with the substrate. Good adhesion is a challenge, namely when a nonwoven substrate is used. Good cohesion ensures that the adhesive does not break, in particular in response to external forces, and namely in response to strain. The adhesive is subject to external forces when the absorbent product has acquired liquid, which is then stored in the absorbent polymer material 110 which in response swells. An exemplary adhesive should allow for such swelling, without breaking and without imparting too many compressive forces, which would restrain the absorbent polymer material 110 from swelling. It may be desirable that the adhesive not break, which would deteriorate the wet immobilization. Exemplary suitable thermoplastic materials can be as described in the already mentioned patent application EP 1447067, particularly at sections [0050] to [0063].

The thermoplastic material, typically a hotmelt adhesive, can be present in the form of fibres throughout the core, being provided with known means, i.e. the adhesive can be fiberized. Typically, the fibres can have an average thickness of about 1 micrometer to about 100 micrometers and an average length of about 5 mm to about 50 cm. In particular, the layer of thermoplastic material, typically e.g. a hot melt adhesive, can be provided such as to comprise a net-like structure.

To improve the adhesiveness of the thermoplastic material 120 to the substrate layer 100 or to any other layer, in particular any other non-woven layer, such layers may be pre-treated with an auxiliary adhesive.

In particular, typical parameters of the hot melt adhesive in accordance with the present invention can be as follows.

In an aspect, the loss angle tan Delta of the adhesive at 60° C. should be below the value of about 1, or below the value of about 0.5. The loss angle tan Delta at 60° C. is correlated with the liquid character of an adhesive at elevated ambient temperatures. The lower tan Delta, the more an adhesive behaves like a solid rather than a liquid, i.e. the lower its tendency to flow or to migrate and the lower the tendency of an adhesive superstructure as described herein to deteriorate or even to collapse over time. This value is hence particularly important if the absorbent article is used in a hot climate.

In a further aspect, hot melt adhesives in accordance with the present invention may have a sufficient cohesive strength parameter $\gamma$. The cohesive strength parameter $\gamma$ is measured using the Rheological Creep Test as referred to hereinafter. A sufficiently low cohesive strength parameter $\gamma$ is representative of elastic adhesive which, for example, can be stretched without tearing. If a stress of $\tau=1000$ Pa is applied, the cohesive strength parameter $\gamma$ can be less than about 100%, less than about 90%, or less than about 75%. For a stress of $\tau=125$ 000 Pa, the cohesive strength parameter $\gamma$ can be less than about 1200%, less than about 1000%, or less than about 800%.

According to the present invention, the substrate layer 100 and the cover layer 130 in the absorbent core 28 can comprise a fibrous web, for example a nonwoven web, comprised of fibres substantially randomly oriented in the X-Y plane, i.e. in the plane defined by the web in a generally flat condition. By "substantially randomly oriented" is meant that, due to processing conditions of the fibrous web, there may be a higher amount of fibres oriented in the machine direction (MD) than the cross direction (CD), or vice-versa. For example, in spunbonding and meltblowing processes continuous strands of fibres are deposited on a support moving in the MD. Despite attempts to make the orientation of the fibres of the spunbond or meltdown nonwoven web truly "random," usually a slightly higher percentage of fibres are oriented in the MD as opposed to the CD.

In the absorbent core 28 of the present invention, the substrate layer 100, or the cover layer 130, or also both of them, comprise a plurality of discrete regions 150 of fibre reorientation, i.e. regions where the fibres of the respective fibrous web are oriented substantially orthogonal to the X-Y plane, i.e. to the plane of the web in a generally flat condition as said above. By saying "oriented substantially orthogonal to the X-Y plane" it is meant that in these discrete regions the fibres are forced, or stretched, or in any case urged, typically by mechanical means, as will be explained in more detail below, out of the plane of the fibrous web, in a direction which is not parallel to said plane, typically in a direction orthogonal thereto. This does not mean that the entirety of fibres in said discrete regions of reorientation are actually oriented orthogonal to the X-Y plane, but at least part of them typically can be. Fibre reorientation, as meant according to the present invention, differs from e.g. embossing or simply pleating a web in that the fibres, and in turn the web, are strained or stretched or in any case forced out of the X-Y plane, which can typically involve the provision of areas of reduced density with respect to the surrounding areas of the web not affected by the fibre reorientation.

Typically, according to the present invention, the discrete regions of fibre reorientation can have a linear orientation defining a longitudinal axis L in the X-Y plane, i.e. they extend along a direction and typically have a length. The discrete regions of fibre reorientation in the substrate layer 100 and/or in the cover layer 130 of the absorbent core 28 of the present invention can be provided with suitable means, typically by performing a mechanical operation, as will be explained in detail with reference to some exemplary embodiments, also typically with the exclusion of means not suitable for providing discrete regions with a linear orientation, such as for example felting with needles which instead can at most somehow displace fibres at point shaped regions, which is not within the scope of the present invention.

The plurality of discrete regions of fibre reorientation can be provided to the substrate layer 100 and/or to the cover layer 130 by ring rolling, or corrugating, selected regions of the respective fibrous web. Suitable processes for ring rolling or "pre-corrugating" are described for example in U.S. Pat. No. 4,107,364 issued to Sisson on Aug. 15, 1978, U.S. Pat. No. 4,153,664 issued to Sabee on May 8, 1979, U.S. Pat. No. 4,517,714, issued to Sneed et al. on May 21, 1985, U.S. Pat. No. 5,143,679 issued to Gerald M. Weber, et al. on Sep. 1, 1992, U.S. Pat. No. 5,156,793 issued to Kenneth B. Buell, et al. on Oct. 20, 1992, and U.S. Pat. No. 5,167,897 issued to Gerald M. Weber, et al. on Dec. 1, 1992.

Alternatively, the substrate layer 100 and/or the cover layer 130 can be provided with the plurality of discrete regions of fibre reorientation 150 by means of SELF technology. Suitable SELFed materials can receive the SELF treatment in appropriate regions in order to have the plurality of discrete regions of fibre reorientation, and can be made for example according to the description in PCT applications WO 95/07675 and WO 95/20932. Typically a SELFed material is modified by mechanical treatment in order to have a strainable network which exhibits elastic-like behaviour without added elastic material, although elasticity is not a required feature in the substrate layer 100 and/or cover layer 130 of the absorbent core 28 of the present invention, the SELF treatment being actually meant to provide the discrete regions of fibre reorientation.

The "fold" lines in the corrugations of a ring rolled fibrous web, or also of a SELFed fibrous web, namely the substrate layer 100, or the cover layer 130, or both, forming the plurality of discrete regions of fibre reorientation, can typically run at least in the longitudinal direction of the absorbent core 28, as illustrated for example in FIG. 1, and explained in more detail further on.

According to an embodiment of the present invention, such as that illustrated in FIGS. 1, 2, 2a, and 3, the absorbent core 28 comprises the substrate layer 100 provided with a plurality of discrete regions 150 of fibre reorientation which comprise a plurality of fibres having portions reoriented in a direction substantially orthogonal to the X-Y plane, i.e. to the plane defined by the web in a generally flat condition. Each discrete region 150 has an apex 160 corresponding in a transverse section to the point of maximum displacement from the X-Y plane. A discontinuous layer of absorbent polymer material 110 and a layer of thermoplastic material 120 are also shown in FIGS. 2 and 3. The fibre reorientation can be typically achieved in the plurality of selected discrete regions 150 by means of ring rolling the fibrous web constituting the substrate layer 100. As described for example in the above mentioned U.S. Pat. No. 4,153,664 or U.S. Pat. No. 4,517,714, ring rolling of the web in selected regions can be typically achieved by feeding the web through e.g. the nip of a pair of toothed meshing rollers, or of interdigitating grooved rolls, such as those respectively illustrated in the above mentioned patents. The geometry of the rolls and the shapes and profiles of the respective grooves or teeth, as well as the mechanical relationship between the cooperating surfaces of the rolls, e.g. the clearance, can be typically selected in order to achieve the desired fibre reorientation in the treated fibrous web, for example the substrate web 100 of FIGS. 1, 2, 2a and 3. The mechanical action of the meshing teeth or grooves typically squeezes and stretches the fibres of the web, as shown in more detail in FIG. 2a, which illustrates for clarity the substrate layer 100 only as present in the dotted circle indicated in FIG. 2. The fibres are then reoriented substantially in the Z-direction, i.e. substantially orthogonally, with respect to the X-Y plane. In areas closer to the apexes 160 the fibres can be actually strained and stretched substantially in the Z-direction, and also substantially at least partially cut at the apexes themselves.

Figure 4A:
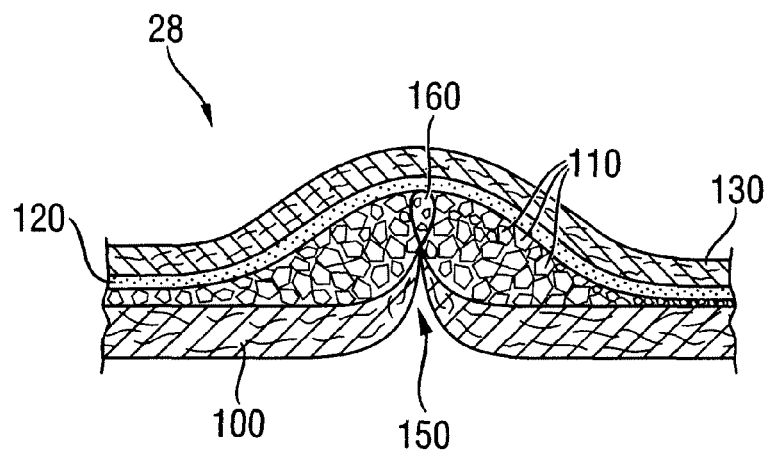
FIG. 4a shows an enlarged detail of the cross section of FIG. 4.

According to the present invention the plurality of discrete regions of fibre reorientation can also be provided in the fibrous web, either the substrate layer 100 or the cover layer 130, or both, of the absorbent core 28, as described for example in PCT applications WO 04/058118, WO 04/058497, and WO 04/059061, assigned to The Procter & Gamble Company. Embodiments of the present invention where the plurality of discrete regions of fibre reorientation can be provided as described in the above mentioned patent applications are illustrated in FIGS. 4, 4a, and 5. Accordingly, the discrete regions of fibre reorientation in the respective fibrous web can be formed by typically urging fibres out of plane substantially in the Z-direction at discrete, localized portions of the fibrous web, forming so called "tufts". The urging out of plane can be due to fibre displacement, i.e., some fibres are able to move relative to other fibres and be "pushed" out of plane. Alternatively, the urging out of plane can be due to the fibres of the "tufts" having been at least partially plastically stretched and permanently deformed to form said "tufts", as described for example more in detail in WO 04/058497.

In FIG. 4, and also in FIG. 4a, depicting as indicated an enlarged detail taken from FIG. 4, an absorbent core 28 is shown, which comprises a substrate layer 100 provided with a plurality of discrete regions 150 of fibre reorientation which comprise a plurality of fibres having portions reoriented in a direction substantially orthogonal to the X-Y plane. Each discrete region 150 has an apex 160, as better shown in FIG. 4a, corresponding to the point of maximum displacement from the X-Y plane. In each region 150 of fibre reorientation the fibres displaced out of the X-Y plane substantially in the Z-direction can form a "tuft", as described in the above mentioned patent applications WO 04/058118, WO 04/058497, and WO 04/059061. A discontinuous layer of absorbent polymer material 110 and a layer of thermoplastic material 120 are also shown in FIGS. 4 and 4a.

According to an embodiment of the present invention, the plurality of fibres having portions reoriented in a direction substantially orthogonal to the X-Y plane, comprised in the plurality of discrete regions 150 of the absorbent core 28, can typically at least in part extend towards the non uniform layer of absorbent polymer material 110, and the respective other fibrous layer of the absorbent core structure as well. This is shown in the embodiments illustrated in FIGS. 2, 3, 4, and 4a described so far, and also in the embodiment of FIG. 5, which will be illustrated in more detail further on.

According to an embodiment of the present invention, at least some of the discrete regions 150 of fibre reorientation can comprise the absorbent polymer material 110 at least partially distributed or intermixed among the reoriented fibres. This is shown for example in FIG. 4a, where absorbent polymer material, which can typically comprise absorbent polymer particles, can be at least partially comprised among the reoriented fibres in the discrete regions 150 of fibre reorientation. When considering for example the alternative embodiment of FIG. 2, the absorbent polymer material can be comprised among the reoriented fibres, for example typically in correspondence of the apexes 160, particularly where the fibres can be partially cut, although this is not actually shown in FIG. 2 owing to the small scale of the drawing. The area of the apexes 160, also with partially cut fibres, is instead shown in more detail in FIG. 2a, which represents the substrate layer 100 only: although not shown, the absorbent polymer material can be distributed among the fibres at least in these apex portions 160, particularly where the fibres can be stretched and at least partially cut, for example by the ring rolling or SELF treatment.

In an embodiment of the present invention, the fibres of either the substrate layer 100 or of the cover layer 130, or of both, which have portions reoriented in a direction substantially orthogonal to the X-Y plane in a plurality of discrete regions, can also extend through the other respective fibrous web of the absorbent core. For example, as illustrated in FIG. 5, the substrate layer 100 can comprise a plurality of discrete regions 150 of fibre reorientation, only one of which is shown in FIG. 5, in turn comprising a plurality of fibres having portions reoriented in a direction substantially orthogonal to the X-Y plane, and moreover extending through the cover layer 130 through a discontinuity, typically for example a cut. The embodiment illustrated in FIG. 5 can be exemplary, and is similar to that of FIGS. 4 and 4a, in that it can be made according to the teaching of e.g. patent applications WO 04/058118, WO 04/058497, and WO 04/059061, already mentioned with reference to said figures. The "tuft" formed by the reoriented fibres is clearly visible in the absorbent core of FIG. 5 extending through the cover layer 130.

According to alternative embodiments of the present invention, either the substrate layer 100, or the cover layer 130, or both the substrate and the cover layer of an absorbent core 28 can comprise a plurality of discrete regions of fibre reorientation, comprising a plurality of fibres having portions reoriented in a direction substantially orthogonal to the X-Y plane. As an example, in the embodiment illustrated in FIG. 5 also the cover layer 130 can have a plurality of discrete regions 170 of fibre reorientation, each region 170 corresponding to a region 150 in the substrate layer. This is due to the particular method for making the structure, but alternatively discrete regions of fibre reorientation can be provided in both the substrate layer and the cover layer with no such symmetry.

The plurality of discrete regions of fibre reorientation can be uniformly distributed on the substrate layer, or on the cover layer, or on both, in the absorbent core according to the present invention. Alternatively, the plurality of discrete regions of fibre reorientation can be localized in certain areas of said fibrous layers, for example in a central region. According to an embodiment of the present invention, the plurality of discrete regions of fibre reorientation can be arranged in discrete areas. An example is illustrated in FIG. 1, where in a cut-out portion of the absorbent core 28 the substrate layer 100 is shown. The substrate layer 100 comprises a plurality of discrete regions 150 of fibre reorientation, in turn arranged in a plurality of discrete areas 180 having in the illustrated embodiment a rhombic shape. Other shapes are alternatively possible for the discrete areas 180, for example circular, or oval, or square, or rectangular, or also irregular. FIG. 1 actually depicts an absorbent article with an absorbent core where the discrete regions 150 of fibre reorientation in the substrate layer 100 can be typically provided as explained with reference to the embodiment of FIGS. 2 and 2a, but the above feature is applicable to all embodiments of the present invention. Typically, the plurality of discrete areas 180 has an overall surface area which can represent from about 35% to about 70%, or from about 40% to about 60%, of the total surface area of the absorbent core.

As already mentioned the discrete regions 150 of fibre reorientation can typically have a linear orientation defining a longitudinal axis L in the X-Y plane, i.e. they extend along a direction and typically have a length. The longitudinal axis L is illustrated in the specific embodiments of FIGS. 1, 3, 4, and 5, where it is shown as substantially parallel to the reference Y-axis. Typically, the axis L in the respective fibrous layer or layers of the absorbent core 28 can be oriented such that it runs parallel to the longitudinal axis of the absorbent article 20 incorporating the core 28, as shown for example in FIG. 1.

In the absorbent core of the present invention the substrate layer 100 and the cover layer 130 can be typically provided from nonwoven materials, for example spunbonded or carded nonwoven materials, or also airlaid materials, such as for example latex and/or thermal bonded airlaid materials.

Exemplary materials for the cover layer 130 can be provided by nonwoven materials comprising synthetic fibres, such as polyethylene (PE), polyethylene terephthalate (PET), polypropylene (PP). As the polymers used for nonwoven production are inherently hydrophobic, they can be typically coated with hydrophilic coatings, for example with durably hydrophilic coatings to provide permanently hydrophilic nonwovens. Other nonwoven materials for the cover layer 130 can comprise composite structures such as a so called SMS material, comprising a spunbonded, a melt-blown and a further spunbonded layer. Basis weights for the materials of the cover layer 130 can typically range from about 5 g/m² to about 80 g/m², or from about 10 g/m² to about 60 g/m², or also from about 20 g/m² to about 40 g/m²

Exemplary materials for the substrate layer 100 can comprise fibrous materials comprising cellulose fibres, typically not more than about 60% by weight of cellulose fibres, or from about 30% to about 50% by weight of cellulose fibres. Examples of fibrous materials for the substrate layer 100 can be nonwoven materials, such as for example carded nonwovens, or more typically airlaid or wetlaid fibrous materials, such as for example latex or thermal bonded airlaid fibrous materials, comprising synthetic and natural fibres, such as for example cellulose fibres. Basis weights for the materials of the substrate layer 100 can typically range from about 10 g/m² to about 120 g/m², or from about 40 g/m² to about 100 g/m², or also from about 50 g/m² to about 80 g/m².

Suitable fibrous materials for the substrate layer 100 and the cover layer 130 can also be selected according to how the discrete regions 150 of fibre reorientation are provided, for example as explained in the patents and patent applications mentioned above with reference to the different possible mechanical treatments.

In certain embodiments of the present invention the absorbent polymer material 110 in the absorbent core 28 is present throughout the area of the absorbent core in an average basis weight of less than about 220 g/m², of less than about 180 g/m², from about 60 g/m² to about 150 g/m², or from about 80 g/m² to about 120 g/m². An average basis weight is typically based on the whole area interested by the layer of absorbent polymer material, hence comprising possible openings included in an e.g. discontinuous layer.

It is believed that the absorbent core of the present invention has an improved capacity for the acquisition, distribution, management and retention of body fluids, particularly complex body fluids such as menses or blood or vaginal discharges, owing to the particular structure and arrangement of its component materials, in addition to the already improved structure stability due to the better immobilization of the absorbent polymer material also when the article is fully or partially liquid loaded. The above advantages are achieved by a core structure which is particularly thin and flexible, and substantially shape stable, hence providing an absorbent article, typically a sanitary napkin, with an increased wearing comfort by being thin and dry.

In the absorbent core of the present invention the presence of the plurality of discrete regions of fibre reorientation in at least one of the substrate layer or the cover layer, where the fibres have portions reoriented in a direction substantially orthogonal to the X-Y plane, i.e. typically substantially in the Z-direction, firstly improves fluid transmission in said Z-direction. Typically the reoriented fibres can at least in part extend towards the non uniform layer of absorbent polymer material, i.e. towards the inner portion of the layered absorbent core structure, as shown in the exemplary embodiments of the present invention of FIGS. 2, 3, 4, 4a, and 5. Said arrangement in fact can promote the fluid communication between the fibrous layer, or layers, comprising the plurality of discrete areas of fibre reorientation, and the layer of absorbent polymer material, in turn employing more efficiently the absorbent capacity of the absorbent core through its entire thickness, and taking better advantage of the particular absorption characteristics of its component materials. In addition, the plurality of areas of fibre reorientation in the respective fibrous layer, either the substrate layer, or the cover layer, or both, can increase locally the contact area between said layer or layers and the absorbent polymer material, particularly when the absorbent polymer material, for example comprising absorbent polymer particles, is comprised at least partially among the reoriented fibres in the regions of fibre reorientation, i.e. typically intermixed therein. This can be clearly visible for example in FIG. 2 and also in FIG. 4, where the contact area between the absorbent polymer material and the respective fibrous layer comprising the plurality of discrete areas of fibre reorientation, namely the substrate layer 100 in the exemplary embodiments illustrated, is greater than it would have been without said discrete areas, for example looking at the areas where no regions of fibre reorientation are present.

Overall greater contact area between the layer of absorbent polymer material and the fibrous layer or layers comprising the plurality of discrete regions of fibre reorientation, and also the same presence of fibres being oriented substantially in the Z-direction of the absorbent core, can significantly improve the fluid acquisition and flow within the absorbent core itself, particularly in the case of complex body fluids such as menses or blood or vaginal discharges, which can be typically difficult to manage in an absorbent structure comprising fibres and absorbent polymer material. Typically, fluid received by an absorbent core according to the present invention, for example initially striking the cover layer 130 in case the absorbent core 28 is comprised in an absorbent article 20 such that, in use, the cover layer 130 faces towards the wearer, i.e. constituting the wearer-facing surface of the absorbent core, can diffuse within the cover layer itself, and at the same time be transferred to the underlying layer of absorbent polymer material. The fluid can then be absorbed by the absorbent polymer material, and, typically in correspondence of the apexes 160 of the regions 150 of fibre reorientation, can be drawn towards the substrate layer 100, where it can also diffuse within its thickness, and possibly be partially redirected upwards to the layer of absorbent polymer material 110 through the neighbouring regions of fibre reorientation 150. Similarly, with a possible alternative embodiment for the absorbent core 28 as that illustrated in FIG. 5, the drawing of the body fluid through the cover layer 130 as the fluid receiving layer can be facilitated at the "tufts" created by the reoriented fibres of the substrate layer 100 partially extending through the cover layer 130.

According to the present invention, the absorbent core can provide a more efficient fluid management, in terms of acquisition, distribution and absorption, as explained above with reference to some exemplary embodiments, which can be particularly useful in case of complex body fluids such as menses or blood. Overall, this increased efficiency in the composite structure according to the present invention can translate in a more effective exploitation of the absorbent capacity of the absorbent polymer material, also in presence of problematic body fluids such as menses or blood or vaginal discharges.

This is achieved in a structure which is typically thin and is capable of employing more completely the absorption capacity of the different materials, which can hence be present in a typically lesser amount, thus also providing a particularly thin structure having improved dimensional stability during absorption and therefore increased comfort during use.

According to an embodiment of the present invention the absorbent polymer material can be selected among the polyacrylate based polymers described in the PCT Patent Application WO2007/047598, which are polyacrylate based materials very slightly crosslinked, or substantially not crosslinked at all, this further improving the above mentioned synergistic effect. Particularly, said polyacrylate based materials can have an extractable fraction of at least about 30% by weight, between about 30% and about 80% by weight, or between about 32% and about 70% by weight, evaluated according to the Extractables test method described in the above referenced application. Alternatively, said polyacrylate based materials can have a retention capacity of at least about 30 g/g, at least about 35 g/g, or at least about 40 g/g, evaluated according to the Centrifuge Retention Capacity test described in the above referenced application. Said polymers in fact are particularly effective in absorbing complex body fluids such as menses or blood, and upon absorption of such fluids do not generally show a marked swelling, followed by gel blocking, like traditional superabsorbents, but rather act to a certain extent as thickeners of the body fluid, immobilizing it as a sort of gelatinous mass within the absorbent structure, for example in the interstices among the fibres, without causing substantial swelling and in turn a sensible increase of the overall thickness of the absorbent core.

According to the present invention, the absorbent core 28 can fully constitute the absorbent element in an absorbent article, or can constitute part of it, being complemented with other layers in a composite structure. Also, an absorbent article comprising an absorbent core according to the present invention can further comprise a fibrous acquisition layer between the absorbent core 28 and the topsheet. According to an embodiment of the present invention the acquisition layer can for example comprise fibrous nonwoven materials made by air laying or wet laying of synthetic fibres such as polyethylene (PE), polyethylene terephthalate (PET), or polypropylene (PP), similarly to the cover layer 130 of the absorbent core 28 of the present invention.

Exemplary materials for the fluid acquisition layer could comprise spunbonded or carded nonwoven materials, or airlaid materials such as for example latex bonded or thermal bonded airlaid materials. Basis weights can typically range from about 10 g/m$^2$ to about 60 g/m$^2$, or from about 25 g/m$^2$ to about 40 g/m$^2$.

According to another embodiment of the present invention the absorbent article can comprise a further fibrous layer comprised between the absorbent core 28 and the backsheet, i.e. typically provided at the garment facing surface of the core. This optional layer can be provided by similar fibrous materials as those already described for the substrate layer 100 of the absorbent core of the present invention. This optional fibrous layer according to this further embodiment of the present invention can act as an added wicking layer receiving and distributing excess fluid which might not be fully retained by the absorbent core 28. The presence of cellulose fibres can make the layer particularly effective in acquiring and diffusing the fraction of body fluids like menses or blood which is not completely absorbed by the absorbent polymer material of the absorbent core 28.

An exemplary process for producing absorbent cores 28 in accordance with the present invention can comprise the following steps.

In one step, the substrate layer 100 is laid onto a formation surface. The absorbent polymeric material 110 is disposed by means known in the art, for example by means of a lay-down drum, in the selected non uniform e.g. discontinuous layer onto the substrate layer 100, optionally after providing a stabilizing adhesive on the substrate layer 100, for example in longitudinal stripes. In a further process step, a hot melt adhesive is placed with known means onto the absorbent polymer material, for example in form of fibres.

While any adhesive application means known in the art can be used to place the hot melt adhesive onto the absorbent polymer material, the hot melt adhesive can be typically applied by a nozzle system. For example, a nozzle system can be utilised, which can provide a relatively thin but wide curtain of adhesive, for example in form of fibres. This curtain of adhesive is than placed onto the substrate layer 100 and the absorbent polymer material 110.

In a further process step, a cover layer 130 can be placed upon the substrate layer 100, the absorbent polymer material and the hot melt adhesive layer. The cover layer 130 will be in adhesive contact with the substrate layer 100 in the areas of junction 140. In these areas of junction 140 the adhesive is in direct contact with the substrate layer 100. The cover layer 130 will typically not be in direct adhesive contact with the substrate layer 100 where the absorbent polymer material 110 is present.

In one alternative embodiment, the cover layer 130 and the substrate layer 100 can be provided from a unitary sheet of material. The placing of the cover layer 130 onto the substrate layer 100 can then involve the folding of the unitary piece of material.

Hence, the uneven service of the lay-down system, which may be a lay-down drum, typically determines the distribution of absorbent polymer material in the non uniform, for example discontinuous layer and likewise can determine the pattern of areas of junction 140. The distribution of absorbent polymer material may be influenced by vacuum means.

The distribution of absorbent polymer material can be profiled, for example profiled in the longitudinal direction, or in the lateral direction, or in both. Hence, for example, along the longitudinal axis of the absorbent core, which is normally coincident with the longitudinal axis of the absorbent article, for example a sanitary napkin, the basis weight of the absorbent polymer material can change. For example, the basis weight of absorbent polymer material in at least one freely selected first square measuring 1 cm×1 cm can be at least 10%, 20%, 30%, 40% or 50% higher than the basis weight of absorbent polymer material in at least one freely selected second square measuring 1 cm×1 cm. Typically the criterion is met if the first and the second square are centred about the longitudinal axis.

Typically the absorbent polymer material for absorbent cores according to the present invention can comprise absorbent polymer particles. Without wishing to be bound by theory it is believed that such material, even in the swollen state, i.e. when liquid has been absorbed, does not substantially obstruct the liquid flow throughout the material, particularly when further the permeability of said material, as expressed by the saline flow conductivity of the absorbent polymer material, is greater than about 10, about 20, about 30 or about 40 SFC-units, where 1 SFC unit is $1\times10^{-7}$ (cm$^3$×s)/g. Saline flow conductivity is a parameter well recognised in the art and is to be measured in accordance with the test disclosed in EP 752 892 B.

The plurality of discrete regions of fibre reorientation can be provided in the substrate layer 100, or in the cover layer 130, or in both, according to mechanical treatment processes described for example in the documents cited with reference to the exemplary embodiments described above, i.e. for example by ring rolling. The respective fibrous layer or layers can be subjected to the mechanical treatment in order to provide the plurality of discrete regions of fibre reorientation before combining the layers together with the other elements in order to form the absorbent core. Alternatively, the plurality of discrete regions of fibre reorientation can be provided in the selected fibrous layer or layers by subjecting the entire structure of the absorbent core, i.e. after formation, to the mechanical treatment. When considering the exemplary embodiment described above, the embodiment illustrated in FIGS. 2 and 3 can be typically provided with the plurality of discrete regions of fibre reorientation by subjecting the selected fibrous layer, namely the substrate layer 100, to the mechanical treatment, for example ring rolling, before the layer is combined with the other elements in the absorbent core 28. In the exemplary embodiments of the present invention illustrated in FIGS. 4, 4*a* and 5 the plurality of discrete regions of fibre reorientation can instead be typically provided by subjecting the already formed multi layer structure of the absorbent core 28 to the mechanical treatment, which in turn may be for example as disclosed in the already referenced patent application WO 04/058947.

Backsheet

The absorbent article comprising the core according to the present invention can also comprise a backsheet 40. The backsheet primarily has to prevent the extrudes absorbed and contained in the absorbent structure from wetting materials that contact the absorbent article such as underpants, pants, pyjamas, undergarments, and shirts or jackets, thereby acting as a barrier to fluid transport. The backsheet according to an embodiment of the present invention can also allow the transfer of at least water vapour, or both water vapour and air through it and thus allow the circulation of air into and water vapour out of the article. The backsheet can typically extend across the whole of the absorbent structure and can extend into and form part or all of side flaps, side wrapping elements or wings, if present.

The elements of the article may be joined by any means suitable for affixing two adjacent layers of material, such that the layers are directly attached to one another or directly attached to one another via the joining means. Suitable joining means include adhesive, fusion bonding, ultrasonic bonding, stitching, heat (e.g. thermo bonding by welding fibres at intersections or melting a polymer to attach fibres or films to each other), embossing, crimping, pressure bonds, dynamic mechanical bonds or combinations thereof.

Especially if the absorbent article finds utility as a sanitary napkin or panty liner, the absorbent article can be also provided with a panty fastening means, which provides means to attach the article to an undergarment. For example the panty fastening means may comprise a panty fastening adhesive on the garment facing surface of the backsheet, or alternatively a mechanical fastener such as hook and loop fasteners such as marketed under the trade name VELCRO, snaps or holders. The panty fastening adhesive provides a means for securing the article to the panty and optionally also a means for securing the article when soiled, to a fold and wrap package for convenient disposal.

The absorbent article comprising the absorbent core of the present invention can be used beneficially in the context of sanitary napkins. The absorbent article may thus also have all those features and parts, which are typical for products in the context of their intended use. For sanitary napkins this includes particularly wings or side flaps which are provided on the side edges of the napkin and which fold around the crotch edge of an undergarment. The side flaps can be provided as extensions of one or several of the elements of the napkin such as the topsheet and/or backsheet. They can also be made separately and be joined to the side margin of the napkin.

Example

A sanitary napkin comprising an absorbent core according to an embodiment of the present invention is similar to that illustrated in FIGS. 1 and 2 and comprises a topsheet constituted by a polyethylene perforated formed film, a backsheet constituted by a 25 g/m² polyethylene film, a core comprising a cover layer constituted by a 30 g/m² carded nonwoven comprising polyester fibres and PP/PE bicomponent fibres, available from BBA Fiberweb under the code TBPL 50/50 6 dpf philic PET/BICO, a discontinuous layer of absorbent polymer material constituted by a particulate superabsorbent material available from Nippon Shokubai under the trade name Aqualic L520 distributed onto the substrate layer in a non uniform layer having overall an average basis weight of 120 g/m², and a layer of thermoplastic material constituted by a hot melt adhesive available from HB Fuller under the trade name NV 1151 Zeropack applied in fibres having an average thickness of about 50 µm at a basis weight of 11 g/m². The absorbent core further comprises a substrate layer, constituted by a 65 g/m² latex bonded airlaid (LBAL) material comprising 30% by weight cellulose fibres, 40% by weight PET fibres and 30% by weight latex binder, available from Concert GmbH under the code WHXX65.

The substrate layer comprises a plurality of discrete areas of fibre reorientation typically provided by ring rolling treatment of the fibrous web constituting the substrate layer, and arranged in discrete areas of rhombic shape as illustrated in FIG. 1. Said discrete areas represent 55% of the total surface area of the absorbent core.

The Rheological Creep Test and the Dynamical Mechanical Analysis (DMA)-Temperature Sweep Test mentioned hereinabove for measuring the cohesive strength parameter γ and the cross-over temperature parameter Tx respectively, are as described in the copending patent application EP 1447067, assigned to the Procter & Gamble Company.

Artificial Menstrual Fluid (AMF)

Artificial Menstrual Fluid is based on modified sheep's blood that has been modified to ensure it closely resembles human menstrual fluid in viscosity, electrical conductivity, surface tension and appearance. It is prepared as explained in U.S. Pat. No. 6,417,424, assigned to The Procter & Gamble Company, from line 33 of column 17 to line 45 of column 18, to which reference is made.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that is alone, or in any combination with any other reference or references, teaches, suggests or discloses any such invention. Further, to the extend that any meaning or definition of term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent core for an absorbent article intended for absorption of menses or blood or vaginal discharges, the core comprising:
    a perimeter;
    a substrate layer including a substrate layer first surface and a substrate layer second surface;
    the absorbent core further including a non uniform layer of absorbent polymer material;
    the non uniform layer of absorbent polymer material including a non uniform layer of absorbent polymer material first surface and a non uniform layer of absorbent polymer material second surface;
    the absorbent core further including a layer of a thermoplastic material;
    the layer of thermoplastic material including a layer of thermoplastic material first surface and a layer of thermoplastic material second surface;
    the absorbent core further including a cover layer including a cover layer first surface and a cover layer second surface wherein the non uniform layer of absorbent polymer material second surface is in at least partial contact with the substrate layer first surface, wherein portions of the layer of thermoplastic material second surface are in direct contact with the substrate layer first surface within the perimeter and portions of the layer of thermoplastic material second surface are in direct contact with the non uniform layer of absorbent polymer material first surface, and wherein the cover layer second surface is in direct contact with the layer of thermoplastic material first surface; and
    the substrate layer and the cover layer each including a fibrous web of fibres substantially randomly oriented with respect to an X-Y plane, wherein the substrate layer or the cover layer comprise a plurality of discrete regions of fibre reorientation, comprising a plurality of fibres having portions reoriented in a direction substantially orthogonal to the X-Y plane.

2. The absorbent core according to claim 1, wherein the portions reoriented in a direction substantially orthogonal to the X-Y plane, at least in part extend towards the non uniform layer of absorbent polymer material.

3. The absorbent core according to claim 1, wherein at least some of the discrete regions of fibre reorientation further comprise the absorbent polymer material among the reoriented fibres.

4. The absorbent core according to claim 1, wherein the absorbent polymer material comprises absorbent polymer particles.

5. The absorbent core according to claim 1, wherein the absorbent core has an area, and wherein the absorbent polymer material is present throughout the area of the absorbent core in an average basis weight of less than about 220 g/m².

6. The absorbent core according to claim 1, wherein the absorbent core has an area, and wherein the absorbent polymer material is present throughout the area of the absorbent core in an average basis weight of less than about 180 g/m².

7. The absorbent core according to claim 1, wherein the absorbent core has an area, and wherein the absorbent polymer material is present throughout the area of the absorbent core in an average basis weight from about 60 g/m² to about 150 g/m².

8. The absorbent core according to claim 1, wherein the absorbent core has an area, and wherein the absorbent polymer material is present throughout the area of the absorbent core in an average basis weight from about 80 g/m² to about 120 g/m².

9. The absorbent core according to claim 1, wherein both the substrate layer and the cover layer comprise a plurality of discrete regions of fibre reorientation, comprising a plurality of fibres having portions reoriented in a direction substantially orthogonal to the X-Y plane.

10. The absorbent core according to claim 1, wherein fibres of the substrate layer having portions reoriented in a direction substantially orthogonal to the X-Y plane extend through the cover layer.

11. The absorbent core according to claim 1, wherein the plurality of discrete regions is uniformly distributed on the substrate layer and/or on the cover layer.

12. The absorbent core according to claim 1, wherein each of the discrete regions has a linear orientation defining a longitudinal axis in the X-Y plane.

13. The absorbent core according to claim 1, wherein the plurality of discrete regions is arranged in discrete areas having a circular, or oval, or square, or rectangular, or rhombic shape.

14. The absorbent core according to claim 1, wherein the non uniform layer of absorbent polymer material is a discontinuous layer of absorbent polymer material.

15. The absorbent core according to claim 1, wherein the direct contact between the portions of the layer of thermoplastic material second surface and the substrate layer first surface creates a discontinuity in the absorbent polymer material.

* * * * *